(12) United States Patent
Fischell et al.

(10) Patent No.: US 9,254,211 B2
(45) Date of Patent: Feb. 9, 2016

(54) STENT DELIVERY SYSTEM USING A STEERABLE GUIDE WIRE

(75) Inventors: David R. Fischell, Fair Haven, NJ (US);
Robert E. Fischell, Dayton, MD (US);
Tim A. Fischell, Kalamazoo, MI (US);
Scott J. S. Fischell, Glenelg, MD (US)

(73) Assignee: Cordis Corporation, Miami Lake, FL (US)

( * ) Notice: Subject to any disclaimer, the term of this patent is extended or adjusted under 35 U.S.C. 154(b) by 2673 days.

(21) Appl. No.: 11/244,777

(22) Filed: Oct. 6, 2005

(65) Prior Publication Data

US 2007/0083253 A1    Apr. 12, 2007

(51) Int. Cl.
*A61F 2/958* (2013.01)
*A61M 25/10* (2013.01)
*A61F 2/95* (2013.01)

(52) U.S. Cl.
CPC . *A61F 2/958* (2013.01); *A61F 2/95* (2013.01); *A61M 25/104* (2013.01); *A61M 2025/1056* (2013.01); *A61M 2025/1063* (2013.01)

(58) Field of Classification Search
CPC .......... A61F 2/958; A61F 2/95; A61M 25/10; A61M 25/1025; A61M 25/104; A61M 2025/1056; A61M 2025/1063; A61M 2025/1093
USPC ......... 606/108, 191, 192, 194, 200; 623/1.11, 623/1.23, 1.24, 1.42; 604/103.03
See application file for complete search history.

(56) References Cited

U.S. PATENT DOCUMENTS

| | | | | |
|---|---|---|---|---|
| 4,545,390 A | * | 10/1985 | Leary | 600/462 |
| 4,719,924 A | * | 1/1988 | Crittenden et al. | 600/585 |
| 4,813,434 A | * | 3/1989 | Buchbinder et al. | 600/585 |
| 4,886,067 A | * | 12/1989 | Palermo | 600/434 |
| 5,002,559 A | * | 3/1991 | Tower | 606/194 |
| 5,040,548 A | * | 8/1991 | Yock | 128/898 |
| 5,060,660 A | * | 10/1991 | Gambale et al. | 600/585 |
| 5,228,453 A | * | 7/1993 | Sepetka | 600/585 |
| 5,275,622 A | * | 1/1994 | Lazarus et al. | 623/1.11 |
| 5,312,340 A | * | 5/1994 | Keith | 604/99.04 |
| 5,333,620 A | * | 8/1994 | Moutafis et al. | 600/585 |
| 5,365,943 A | * | 11/1994 | Jansen | 600/585 |
| 5,411,476 A | * | 5/1995 | Abrams et al. | 604/95.01 |
| 5,417,658 A | * | 5/1995 | Loney et al. | 604/102.02 |
| 5,421,349 A | * | 6/1995 | Rodriguez et al. | 600/585 |
| 5,429,139 A | * | 7/1995 | Sauter | 600/585 |
| 5,454,788 A | * | 10/1995 | Walker et al. | 604/99.04 |
| 5,547,472 A | * | 8/1996 | Onishi et al. | 604/103.01 |

(Continued)

FOREIGN PATENT DOCUMENTS

EP    0343509    11/1989
EP    1493403 A1    1/2005

(Continued)

*Primary Examiner* — Dianne Dornbusch

(57) ABSTRACT

A thin-walled guide wire tube is fixedly and sealably attached to both a proximal section and a distal section of a balloon angioplasty catheter. A stent is co-axially mounted onto the inflatable balloon of the balloon angioplasty catheter. Because the guide wire tube forms an inner liner for the balloon angioplasty catheter, the fluid inflation lumen of the catheter is sealed so the inflation liquid that pressurizes the balloon will not leak as it would be if there were no "inner liner" and the balloon angioplasty catheter were attached to the guide wire itself. By not having a traditional inner shaft through which a conventional guide wire slides, the deflated balloon on which the stent is mounted can have a reduced diameter.

17 Claims, 3 Drawing Sheets

(56) References Cited

U.S. PATENT DOCUMENTS

| | | | |
|---|---|---|---|
| 5,603,721 A | 2/1997 | Lau et al. | |
| 5,634,928 A * | 6/1997 | Fischell et al. | 623/1.11 |
| 5,639,274 A * | 6/1997 | Fischell et al. | 604/96.01 |
| 5,669,932 A * | 9/1997 | Fischell et al. | 606/198 |
| 5,730,698 A * | 3/1998 | Fischell et al. | 600/3 |
| 5,735,859 A * | 4/1998 | Fischell et al. | 606/108 |
| 5,746,745 A | 5/1998 | Abele et al. | |
| 5,766,152 A * | 6/1998 | Morley et al. | 604/103.1 |
| 5,766,203 A | 6/1998 | Imran et al. | |
| 5,792,144 A * | 8/1998 | Fischell et al. | 606/108 |
| 5,840,081 A | 11/1998 | Andersen et al. | |
| 5,891,154 A | 4/1999 | Loeffler | |
| 5,902,266 A | 5/1999 | Leone et al. | |
| 6,071,285 A | 6/2000 | Lashinski et al. | |
| 6,375,660 B1 * | 4/2002 | Fischell et al. | 606/108 |
| 6,475,167 B1 * | 11/2002 | Fleming et al. | 600/585 |
| 6,544,217 B1 | 4/2003 | Gulachenski | |
| 6,736,827 B1 * | 5/2004 | McAndrew et al. | 606/194 |
| 7,011,673 B2 * | 3/2006 | Fischell et al. | 623/1.11 |
| 7,144,422 B1 * | 12/2006 | Rao | 623/1.42 |
| 2002/0052639 A1 * | 5/2002 | Fischell et al. | 623/1.11 |
| 2002/0147491 A1 * | 10/2002 | Khan et al. | 623/1.11 |
| 2003/0130716 A1 | 7/2003 | Weber et al. | |
| 2004/0193205 A1 | 9/2004 | Burgermeister | |

FOREIGN PATENT DOCUMENTS

| | | |
|---|---|---|
| EP | 1525897 | 4/2005 |
| EP | 1493403 | 2/2006 |
| EP | 1525897 B1 | 11/2011 |
| WO | WO 97/21400 | 6/1997 |
| WO | WO 03/059206 A1 | 7/2003 |
| WO | WO 2004/105646 | 12/2004 |

* cited by examiner

STENT DELIVERY SYSTEM USING A STEERABLE GUIDE WIRE

FIELD OF USE

This invention is in the field of devices for percutaneous insertion into a vessel of the human body to place a stent at the site of an obstruction.

BACKGROUND OF THE INVENTION

Stents are well known devices for placement in vessels of the human body to obtain and maintain patency of that vessel. The greatest use for stents has been for placement within a stenosis in a coronary artery. When a stent is used for treating a coronary artery stenosis, it has always been necessary to first place a guide wire through the stenosis. The next step in the stenting procedure is typically to pre-dilate the stenosis with a balloon angioplasty catheter that is advanced over that guide wire. The balloon angioplasty catheter is then removed and a stent delivery system that includes the stent is advanced over the guide wire and the stent is then deployed at the site of the dilated stenosis.

Recent improvements in the design of stent delivery systems have made it possible to eliminate the step of pre-dilatation for the treatment of many classes of stenoses. The delivery of a stent to the site of a stenosis without pre-dilatation has been given the name "direct stenting". However, even with direct stenting, a guide wire is still required as a precursor to advancing the stent delivery system over that guide wire to place the stent at the site of a stenosis. Placing the guide wire requires additional procedure time and additional cost for the procedure.

In U.S. Pat. No. 6,375,660, Fischell et al. describe a stent delivery system with a fixed guide wire that is not steerable. This fixed, not steerable, guide wire system will not be as capable for rapid delivery of the stent through the tortuous coronary arteries as stent delivery systems that are advanced over a steerable guide wire.

SUMMARY OF THE INVENTION

The present invention is a stent delivery system that uses a steerable guide wire that is coaxially enclosed for most of its length in a guide wire tube. A thin-walled guide wire tube is fixedly and sealably attached to both a proximal section and a distal section of a balloon angioplasty catheter. A stent is co-axially mounted onto the inflatable balloon of the balloon angioplasty catheter. Because the guide wire tube forms an inner liner for the balloon angioplasty catheter, the fluid inflation lumen of the catheter is sealed so the inflation liquid that pressurizes the balloon will not leak as it would be if there were no "inner liner" and the balloon angioplasty catheter were attached to the guide wire itself. By not having a traditional inner shaft through which a conventional guide wire slides, the deflated balloon on which the stent is mounted can have a reduced diameter. Therefore, the outside diameter of the pre-deployed stent mounted onto that balloon is also minimized. This provides a minimum profile, i.e., a minimum outside diameter, for the stent.

A minimum profile at the distal section of the stent delivery system is highly advantageous for improving the percentage of cases that can be treated by means of direct stenting; i.e., without requiring pre-dilation of, a stenosis.

Another advantage of the present invention is that a separate guide wire is eliminated thus saving the cost of such a guide wire. Additionally, the time to perform a stent delivery procedure is reduced because a separate guide wire does not have to be placed prior to using the stent delivery system to place the stent at the site of a stenosis.

The present invention uses a steerable guide wire that extends for the entire length of the stent delivery system. A distal portion of the steerable guide wire can have its shaped changed after it is placed in the patient's vascular system by manipulation of the proximal portion of the steerable guide wire. Thus the shape of the guide wire's distal portion can be straight or highly curved or any curvature in between. This is a great advantage for getting the distal end of the steerable guide wire into the vessel that is to be stented more efficiently as compared to the use of a conventional guide wire.

An important feature of the present invention is a thin-walled, guide wire tube that extends for essentially the entire length of the balloon angioplasty catheter. The guide wire tube is fixedly and sealably attached at its proximal end and its distal end to the balloon angioplasty catheter. Specifically, the guide wire tube forms a liquid tight seal at its proximal end with the proximal fitting of the balloon angioplasty catheter and also a liquid tight seal at its distal end with the balloon onto which the stent is mounted.

Another important aspect of the present invention is the distal seal that is attached to the cylindrical distal end of the balloon and also the distal end of the guide wire tube. This seal is lubricity coated and also has a taper at a small angle in the distal direction that acts like a wedge to open a tight stenosis (sometimes called "Dottering") in an artery. The outer diameter of the distal seal and the cylindrical distal section of the balloon are optimally equal to or slightly larger than the outer diameter of the stent as it is crimped onto the balloon prior to deployment of the stent. This diameter of the cylindrical distal section of the balloon and the distal seal, and the lubricity coating of the conical front surface of the distal seal, together provide the least resistance for pushing through a tight stenosis. Also, the pushability of the combined steerable guide wire and balloon angioplasty catheter work together to get the stent to be pushed through a tight stenosis.

It is envisioned that the guide wire tube would be fixedly attached to the guide wire at one or more locations. The attachment could be by either the use of an adhesive and/or by shrinking the guide wire tube down onto the outer surface of the guide wire to minimize the diameter of the stent delivery system.

It is also envisioned that instead of using a thin-walled guide wire tube to form a sealed inner liner for the inflation lumen of the balloon angioplasty catheter, the guide wire itself could be coated with a polymer to form a water tight seal. The polymer coating would then be sealed to the balloon angioplasty catheter at its proximal and distal ends. This embodiment while more difficult to produce would have a potentially smaller diameter than the embodiment using a separate tube shrunk down onto the guide wire's outer surface.

Thus, the present invention provides a means for placing a stent within a vessel of the human body without requiring a separate guide wire, thus saving the cost of the guide wire and also saving the time required to place a separate guide wire through an obstruction such as an arterial stenosis.

The invention reduces the outside diameter (i.e., the profile) of the distal section of the stent delivery system so as to optimize the capability of the stent delivery system for direct stenting.

This invention provides a steerable guide wire such that the shape of its distal portion can be altered by a means at the guide wire's proximal portion, the changing shape providing better access to a particular coronary artery into which the stent is to be guided. The steerable guide wire and the balloon angioplasty catheter combine in such a manner as to enhance the pushability of the entire stent delivery system. Further, a highly tapered, lubricity coated, distal seal that attaches to the distal end of the balloon of the balloon angioplasty catheter, which tapered distal seal is designed to open a tight stenosis to provide easier passage for the stent mounted onto the balloon. Finally, the outer diameter of the cylindrical distal section of the balloon and the distal seal to be equal to or slightly larger than the diameter of the stent as crimped onto the balloon so as to provide easier passage for the stent through a tight stenosis.

DETAILED DESCRIPTION OF THE INVENTION

Figure 1:
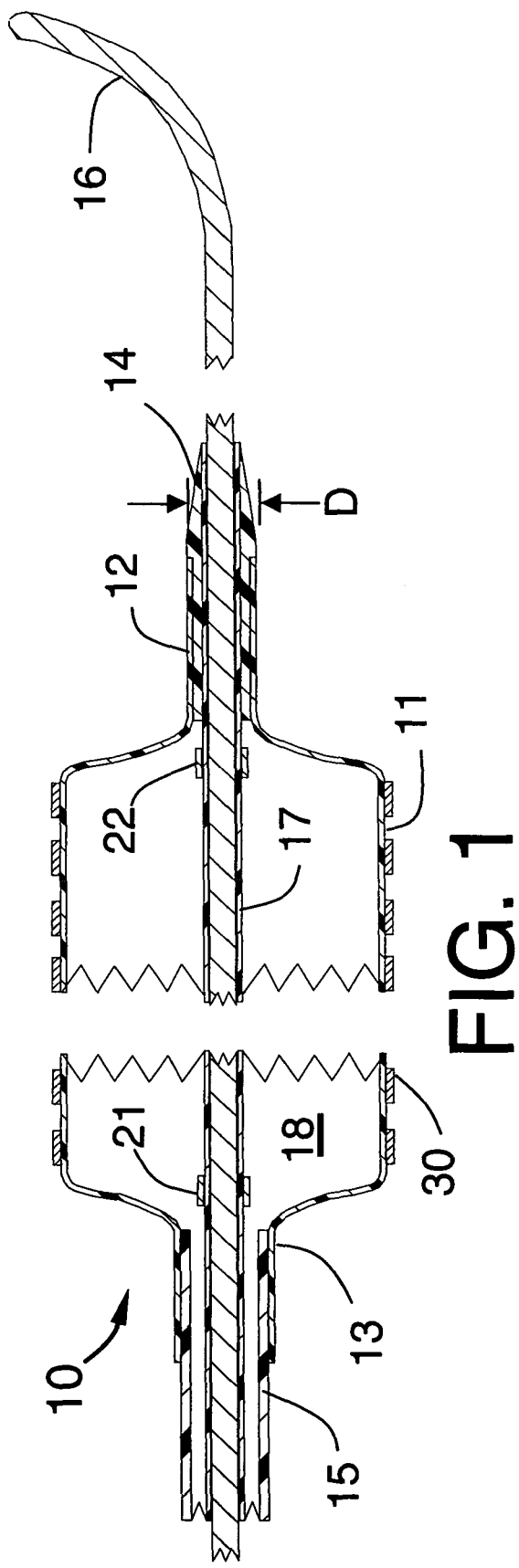
FIG. 1 is a longitudinal cross section of a distal portion of the stent delivery system having a balloon angioplasty catheter mounted co-axially over a steerable guide wire.
Figure 2:
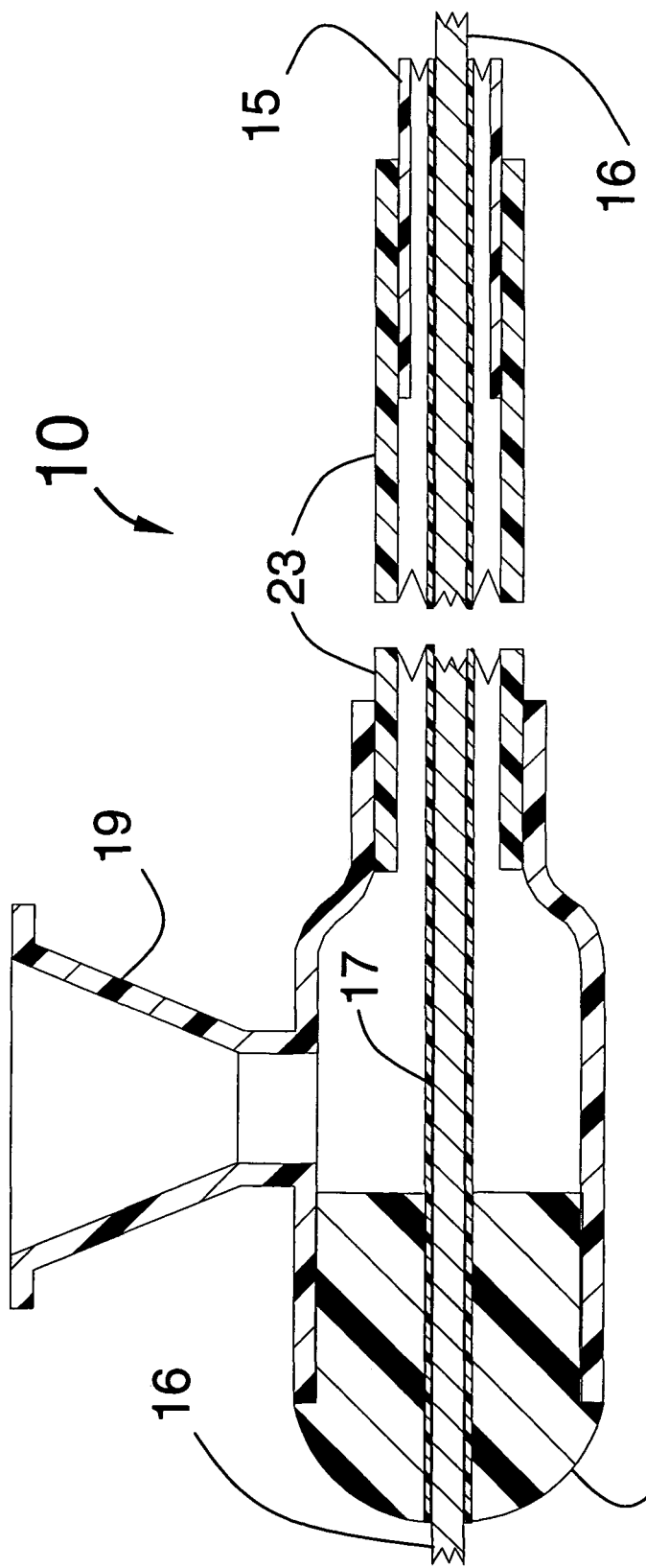
FIG. 2 is a longitudinal cross section of the proximal portion of the stent delivery system that is shown in FIG. 1 utilizing a proximal seal.
Figure 3:
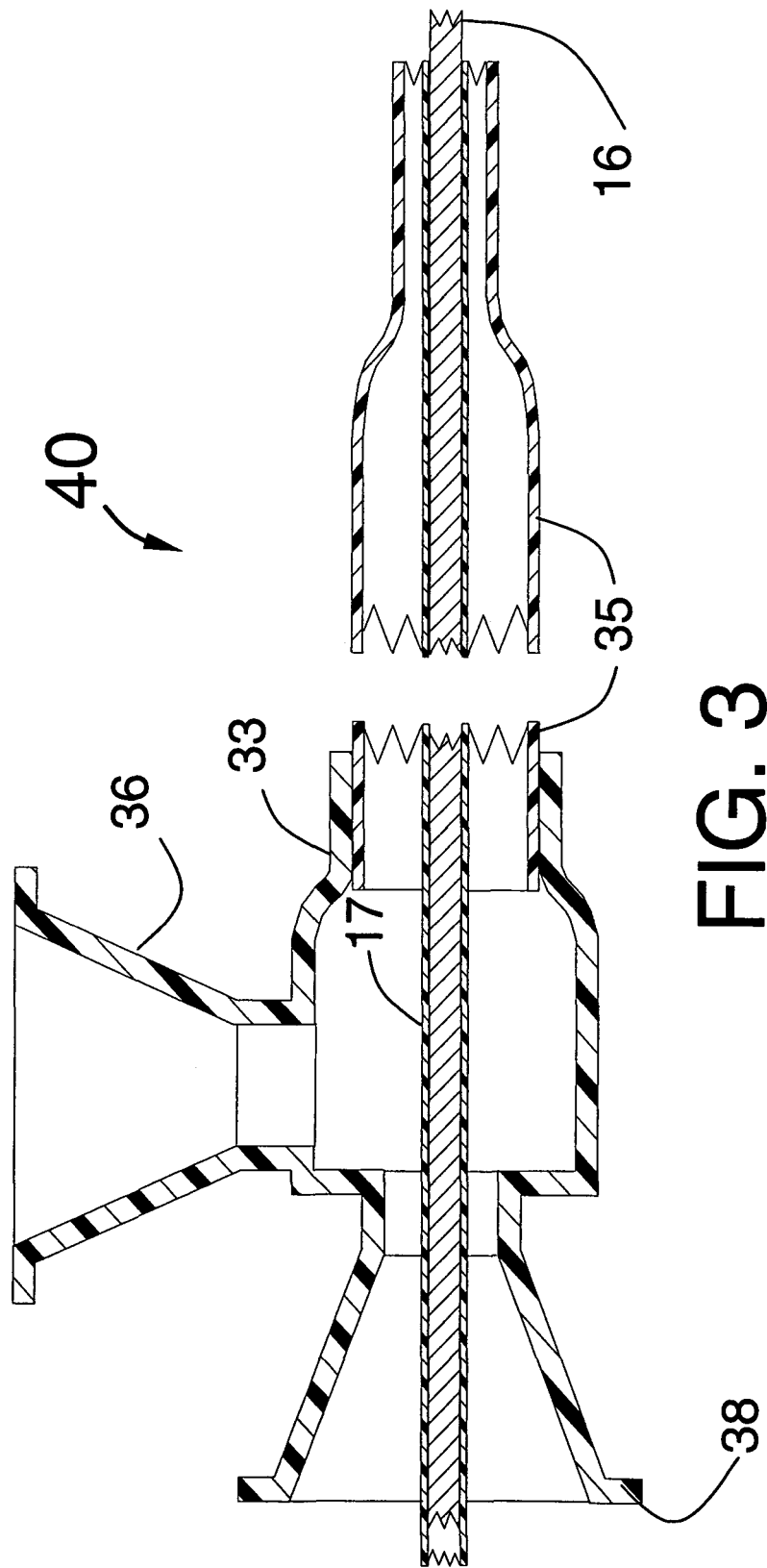
FIG. 3 is a longitudinal cross section of the proximal portion of the stent delivery system that is shown in FIG. 1 utilizing a Luer fitting onto which a hemostasis valve can be placed to seal pressurized fluid for inflating the balloon of the balloon angioplasty catheter.

FIGS. 1, 2 and 3 illustrate a stent delivery system 10 having a fixed but steerable guide wire 16 that is placed within a guide wire tube 17. The distal end and proximal end of the guide wire tube 17 can be joined by a small amount of adhesive to fixedly attach the guide wire tube 17 to the steerable guide wire 16 to prevent the guide wire from moving longitudinally within the stent delivery system 10. The guide wire 16 would typically have a diameter that lies between 0.010 and 0.038 inches. The optimum diameter for use in coronary arteries will be approximately 0.014 inches.

FIG. 1 is a longitudinal cross section of a proximal portion of the stent delivery system 10 showing an inflated balloon 11 onto which the stent 30 is mounted, the balloon having a cylindrical distal section 12 that is fixedly attached to the distal seal 14 and the balloon 11 also having a cylindrical proximal section 13 that is fixedly attached to the distal end of the distal shaft 15. The distal seal 14 is sealed to the distal end of the guide wire tube 17 that surrounds the guide wire 16. The proximal radiopaque marker band 21 and the distal radiopaque marker band 22 are used in a conventional manner to indicate to the operator by fluoroscopy the location of the proximal end and distal end of the stent 30. These marker bands 21 and 22 assist the operator in accurately placing the stent 30 at a proper site within a stenosis of a coronary artery.

The distal seal 14 is fixedly and sealably attached to both the distal cylindrical section 12 of the balloon 11 and the distal end of the guide wire tube 17. In this manner, pressurized liquid for inflating the balloon 11 (and thereby deploying the stent 30) is sealed within the stent delivery system 10. The distal seal 14 also has other design features to assist in placement of the stent 30 into a tight stenosis of a coronary (or other) artery. Specifically, the tapered front conical surfaces of the distal seal 14 and the guide wire tube 17 are both lubricity coated to assist in having the system pushed through a tight stenosis. Also the taper angle is typically less than 30 degrees and optimally less than 15 degrees. Another feature of this invention is that the outer diameter "D" of the cylindrical distal section 12 of the balloon 11 and the distal seal 14 are optimally designed to be approximately equal to or slightly greater in diameter as compared to the outer diameter of the stent 11 as it is crimped or heat nested onto the balloon 11 in its pre-deployed state. For example, if the outer diameter of the stent 11 as crimped onto the balloon 11 before it is inflated is (let us say) 0.7 mm, then the diameter "D" should be approximately 0.7 mm±0.2 mm. Another concept is that the diameter "D" would be optimally between 0.7 and 0.9 mm; i.e., the diameter "D" should be the same dimension as the outer diameter of the crimped stent 30 and possibly the diameter "D" should be as much as 0.2 mm larger than the outer diameter of the crimped stent 30. This inventive concept of having a lubricity coated distal seal 14 with a small cone angle that is attached to the cylindrical distal section 12 of the balloon 11 and having a diameter at least as large as the diameter of the pre-deployed stent 30 can enhance the ability of the stent delivery system 10 to have the pre-deployed stent 30 pushed through even a tight arterial stenosis.

It should be understood that the length of the steerable guide wire 16 that extends beyond the distal end of the distal seal 14 should optimally be less than 5 cm. It should also be understood that the wall thickness for the guide wire tube 17 is less than 0.002 inches and optimally approximately 0.0005 inches.

FIG. 2 is a longitudinal cross section of a proximal portion of the stent delivery system 10 which shows the distal shaft 15 being sealably and fixedly joined to a proximal shaft 23. FIG. 2 also shows the proximal shaft 23 being joined to a Luer fitting 19 that is used to connect a source of a liquid for inflating and deflating the balloon 11 of the stent delivery system 10. The liquid used with such a stent delivery system 10 is typically contrast medium diluted with normal saline solution. Also shown in FIG. 2 is a proximal seal 20 that is fixedly and sealably attached to the Luer fitting 19 and the guide wire tube 17 that is placed around the steerable guide wire 16. The length of the distal shaft 15 would be between approximately 1 cm and 20 cm. The length of the proximal shaft 23 would be typically more than 100 cm. The reason for having the smaller diameter distal shaft 15 is to improve the flexibility of the stent delivery system 10 near its distal end. The reason why the proximal shaft 23 has a larger diameter is to improve liquid flow for inflating and deflating the balloon 11 for deployment of the stent 30. It should be understood that a shaft of a single diameter could be used for this invention.

FIG. 3 (like FIG. 2) shows the distal portion of a stent delivery system 40 with the distal shaft and the proximal shaft formed as a single shaft 35 which is joined to the Luer fitting 33. The shaft 35 is formed from a single plastic tube with most of its length being of a larger diameter and its distal extent of 1 cm to 20 cm in length being of a smaller diameter. FIG. 3 differs from FIG. 2 in that there are two Luer fittings 36 and 38. The Luer fitting 36 is used to inject and remove the balloon inflation liquid. The Luer fitting 38 is designed to have a hemostasis valve (not shown) attached to seal the inflation liquid within the balloon angioplasty catheter. Such a hemostasis valve could be tightened down onto the guide wire tube 17 to form a liquid-tight seal prior to inflating the balloon 11.

The guide wire tube 17 could be solvent swelled for placement over the outer surface of the steerable guide wire 16. As the solvent leaves the plastic of the guide wire tube 17, the final inside diameter of the guide wire tube 17 would be essentially the same diameter as the outer diameter of the guide wire 16. Another method for attaching the guide wire tube 17 to the guide wire 16 would be by shrink fitting the guide wire tube 17 onto the outer surface of the steerable guide wire 16. For the guide wire 16 to be steerable, the outer coil of that guide wire 16 cannot be forced against the inner core of the guide wire 16 but it should exert a gentle pressure so that the steerable guide wire 16 cannot slide easily within the guide wire tube 17. Thus, in its pre-deployed state, with no liquid pressure within the stent delivery system 10, the inner surface of the guide wire tube 17 can gently press against the outer surface of the steerable guide wire 16 but it cannot exert a large force against the outer surface of the guide wire 16. Therefore, in its pre-deployed state, the stent delivery system 10 can steer the steerable guide wire 16 into the artery where the stent 30 is to be placed. When the pre-deployed stent 30 is in place within an arterial stenosis, it can be deployed under a high liquid pressure (typically 8 to 20 atms.) and during that time, the steerable guide wire 16 will not be steerable because of the high force of guide wire tube 17 against the outer coil of the steerable guide wire 16. Such a high pressure would create a high frictional force between the outer coil and the core wire of the steerable guide wire 16. Since no steering is necessary at that time, this is not a detriment to the operation of the stent delivery system 10.

It is also envisioned that instead of using a thin-walled guide wire tube 17 to form a sealed inner liner for the inflation lumen of the balloon angioplasty catheter, the guide wire 16 could be coated with a polymer to form a water tight seal. The polymer coating would then be sealed to the balloon angioplasty catheter 10 at its proximal and distal ends. This embodiment, while more difficult to produce, would have a potentially smaller diameter than the embodiment using a separate guide wire tube 17 shrunk down onto the guide wire 16.

An important goal of this invention is to have an outer diameter of the pre-deployed stent 30 to be no greater than 0.8 mm. As such, it would present one of the lowest profiles for any stent that is used to treat an arterial stenosis. The diameter of the deployed stent 30 could be in the range from as small as 1.5 mm to as large as 6 mm. The larger diameter stents 30 would have a larger pre-deployed diameter because of the increased thickness of the pre-deployed balloon 11. A wall thickness of the stent would optimally be between 0.0015 and 0.004 inches. Furthermore, the optimal type of stent 30 would be a drug eluting stent with a drug such as sirolimus or paclitaxel or any other drug that decreases neointimal hyperplasia subsequent to balloon deployment. The optimum stent would be formed from a high density (i.e. radiopaque) metal such as tantalum or a cobalt-chromium alloy such as L605.

Various other modifications, adaptations, and alternative designs are of course possible in light of the above teachings. Therefore, it should be understood at this time that within the scope of the appended claims, the invention might be practiced otherwise than as specifically described herein.

What is claimed is:

1. A stent delivery system for placing a stent into a vessel of a human subject, the stent delivery system including:
   a balloon angioplasty catheter having a distal portion with an inflatable balloon located at that distal portion, and a proximal portion located externally to the human subject;
   a balloon expandable stent co-axially mounted onto the inflatable balloon, the stent being designed for opening a stenosed vessel of the human subject and the inflatable balloon having a cylindrical distal section and a cylindrical proximal section;
   a steerable guide wire co-axial within and sealably attached to a polymer guide wire tube to prevent longitudinal motion of the steerable guide wire within the polymer guide wire tube, a length of steerable guide wire extending distally beyond the distal portion of the balloon catheter, a distal portion of the steerable guide wire configured to have its shape changed after it is placed in the human subject's vascular system by manipulation of a proximal portion of the steerable guide wire located externally to the human subject; and
   a distal seal having an inner diameter and an outer diameter and a largest outer diameter, the inner diameter of the distal seal fixedly and sealably attached to the polymer guide wire tube, the outer diameter fixedly and sealably attached to the cylindrical distal section of the inflatable balloon, the largest outer diameter distal to the cylindrical distal section of the balloon, and the largest outside diameter of the distal seal is distal to the cylindrical distal section of the inflatable balloon and approximately equal to or slightly greater than the outer diameter of the pre-deployed stent to enhance the ability of the stent to penetrate a tight stenosis.

2. The stent delivery system of claim 1 including a proximal shaft that extends for most of the length of the stent delivery system, the distal end of the proximal shaft being joined to a distal shaft having a distal end that is fixedly attached to the cylindrical proximal section of the inflatable balloon, the proximal shaft having a larger diameter as compared to the diameter of the distal shaft.

3. The stent delivery system of claim 1 where the steerable guide wire has an outside diameter that is less than 0.038 inches.

4. The stent delivery system of claim 1 where the steerable guide wire has an outside diameter of approximately 0.014 inches.

5. The stent delivery system of claim 1 wherein the length of the steerable guide wire extending beyond the distal portion of the balloon catheter is less than 5 cm.

6. The stent delivery system of claim 1 where the stent is a drug eluting stent.

7. The stent delivery system of claim 6 where the drug that is being eluted is sirolimus.

8. The stent delivery system of claim 6 where the drug that is being eluted is paclitaxel.

9. The stent delivery system of claim 1 where the distal seal has a taper in the distal direction that is less than 30 degrees relative to the longitudinal axis of the steerable guide wire, the taper being designed to improve the ability of the distal seal to penetrate a tight stenosis.

10. The stent delivery system of claim 1 where the distal seal has a taper in the distal direction that is less than 15 degrees relative to the longitudinal axis of the steerable guide wire, the taper being designed to improve the ability of the distal seal to penetrate a tight stenosis.

11. The stent delivery system of claim 1 where the outside diameter of the cylindrical distal section of the inflatable balloon is approximately equal to or slightly greater than the outer diameter of the pre-deployed stent to enhance the ability of the stent to penetrate a tight stenosis.

12. The stent delivery system of claim 1 including a proximal seal that is sealably and fixedly attached to a proximal end of the polymer guide wire tube.

13. The stent delivery system of claim 1 where the stent mounted on the balloon of the stent delivery system is formed from a high-density metal selected from the group consisting of tantalum and L605.

14. The stent delivery system of claim 1, wherein the polymer guide wire tube is heat shrunk onto the steerable guide wire.

15. The stent delivery system of claim 1, wherein the polymer guide wire tube is first solvent swelled prior to it being placed onto the steerable guide wire.

16. The stent delivery system of claim 1, further comprising a Luer fitting that is placed at the proximal portion of the balloon angioplasty catheter, the Luer fitting having a pressure tight seal that is fixedly and sealably attached to the polymer guide wire tube.

17. The stent delivery system of claim 16 further comprising a hemostasis valve that is the pressure tight seal that is used to seal the proximal end of the polymer guide wire tube.

* * * * *